US009585799B2

United States Patent
Nordlinder et al.

(10) Patent No.: US 9,585,799 B2
(45) Date of Patent: Mar. 7, 2017

(54) DISPOSABLE BELT HAVING DETACHABLE HOOK AND LOOP FASTENER

(75) Inventors: Jesper Nordlinder, Mölndal (SE); Kent Hermansson, Göteborg (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 50 days.

(21) Appl. No.: 14/411,130

(22) PCT Filed: Jun. 28, 2012

(86) PCT No.: PCT/SE2012/050735
§ 371 (c)(1),
(2), (4) Date: Dec. 24, 2014

(87) PCT Pub. No.: WO2014/003619
PCT Pub. Date: Jan. 3, 2014

(65) Prior Publication Data
US 2015/0297425 A1 Oct. 22, 2015

(51) Int. Cl.
*A61F 13/56* (2006.01)
*A61F 13/62* (2006.01)
(Continued)

(52) U.S. Cl.
CPC ............ *A61F 13/565* (2013.01); *A61F 13/56* (2013.01); *A61F 13/622* (2013.01);
(Continued)

(58) Field of Classification Search
CPC ................ A61F 13/00004; A61F 13/56; A61F 13/5605; A61F 13/5622; A61F 13/565;
(Continued)

(56) References Cited

U.S. PATENT DOCUMENTS 2,891,545 A * 6/1959 Teague .................. A41B 9/002
2/406
4,546,879 A 10/1985 Viscasillas
(Continued)

FOREIGN PATENT DOCUMENTS

CN 2688268 Y 3/2005
EP 0122981 A2 10/1984
(Continued)

OTHER PUBLICATIONS

English-language translation of an Chinese Office Action / Examination report dated Dec. 3, 2015 issued in corresponding Chinese patent application No. 201280073695.5 (6 pages).
(Continued)

*Primary Examiner* — Kathryn E Ditmer
(74) *Attorney, Agent, or Firm* — Drinker Biddle & Reath LLP

(57) ABSTRACT

A disposable belt for use with an absorbent product and a belt system is provided. The disposable belt includes a length of belt material and a hook material patch connected to a first surface portion. The length of belt material has a first major surface and an opposite second major surface, and includes a loop surface structure. The hook material patch is flat and has a first side facing away from the first surface portion, and a second side abutting against the first surface portion. The first side is provided with a first hook surface structure. The second side of the hook material patch is provided with a second hook surface structure, and the second hook surface structure engages with the loop surface structure. The belt system includes the disposable belt and a second length of belt material.

20 Claims, 2 Drawing Sheets

(51) Int. Cl.
*A61F 13/64* (2006.01)
*A61F 13/66* (2006.01)

(52) U.S. Cl.
CPC ............ *A61F 13/625* (2013.01); *A61F 13/64* (2013.01); *A61F 13/66* (2013.01)

(58) Field of Classification Search
CPC ...... A61F 13/62; A61F 13/622; A61F 13/625; A61F 13/64; A61F 2013/5666; A61F 5/01; A61F 5/02; A61F 5/026; A61F 5/028; A61F 5/3738; A61F 15/00; A61F 15/06; A61F 15/006; A61F 9/027; A61F 13/66; A41F 9/00; A41F 9/002; A41F 9/02; A41F 9/025; A41F 1/00; A41F 15/02; A41F 15/002; A41F 17/00; A61B 5/6831; A61M 16/0683; A41D 13/0007; A41D 13/1245; A41D 20/00; A61H 2011/005; A41C 3/0028; A45F 3/047; A42C 5/02; A45C 13/30; A42B 3/08; A61G 13/123; A62B 18/084; A62B 35/00
See application file for complete search history.

(56) References Cited

U.S. PATENT DOCUMENTS

| | | | |
|---|---|---|---|
| 4,555,244 A * | 11/1985 | Buell | A61F 13/622 604/385.26 |
| 4,964,860 A | 10/1990 | Gipson et al. | |
| 4,973,326 A | 11/1990 | Wood et al. | |
| 4,994,054 A | 2/1991 | Pigneul et al. | |
| 5,135,522 A | 8/1992 | Fahrenkrug et al. | |
| 5,362,303 A * | 11/1994 | Jasen | A61F 13/126 128/858 |
| 5,374,262 A | 12/1994 | Keuhn, Jr. et al. | |
| 5,548,871 A * | 8/1996 | Trethewey | A44B 18/00 24/16 R |
| 5,906,604 A | 5/1999 | Rönnberg et al. | |
| 5,971,970 A | 10/1999 | Carlbark et al. | |
| 6,296,164 B1 * | 10/2001 | Russo | A61F 5/449 224/581 |
| 2002/0038110 A1 * | 3/2002 | Kusibojoska | A61F 13/64 604/392 |
| 2002/0045880 A1 * | 4/2002 | Ronnberg | A61F 13/625 604/391 |
| 2002/0116799 A1 * | 8/2002 | Martin | A44B 18/0061 24/452 |
| 2003/0120253 A1 * | 6/2003 | Wentzel | A61F 13/64 604/392 |
| 2004/0153045 A1 | 8/2004 | Baskerville | |
| 2005/0192555 A1 * | 9/2005 | Thomas | A61F 13/505 604/402 |
| 2009/0018515 A1 | 1/2009 | Perry | |
| 2009/0165922 A1 * | 7/2009 | Kingsford | A61B 5/02233 156/66 |
| 2010/0319167 A1 | 12/2010 | Nirmel | |
| 2011/0088225 A1 * | 4/2011 | Fernandez | A44B 18/0069 24/450 |

FOREIGN PATENT DOCUMENTS

| | | | |
|---|---|---|---|
| EP | 0409307 A2 | 1/1991 | |
| EP | 0605013 A1 | 7/1994 | |
| FR | 2830726 A1 | 4/2003 | |
| GB | 989872 A | 4/1965 | |
| GB | 2277865 A | 11/1994 | |
| GB | 2277866 A | 11/1994 | |
| JP | 2005-111119 A | 4/2005 | |
| JP | 2006-325939 A | 12/2006 | |
| SE | WO 2007149017 A1 * | 12/2007 | ........ A61F 13/49011 |
| WO | WO 2009/043101 A1 | 4/2009 | |

OTHER PUBLICATIONS

Extended European search report dated Feb. 12, 2016 issued in corresponding European patent application No. EP 12 87 9769.3 (6 pages).

* cited by examiner

DISPOSABLE BELT HAVING DETACHABLE HOOK AND LOOP FASTENER

CROSS-REFERENCE TO PRIOR APPLICATION

This application is a §371 National Stage Application of PCT International Application No. PCT/SE2012/050735 filed Jun. 28, 2012, which is incorporated herein in its entirety.

TECHNICAL FIELD

The present disclosure relates to a disposable belt for use with an absorbent product. The disclosure further relates to a belts system including a disposable belt.

BACKGROUND

Absorbent products such as products used for incontinence care are in some embodiments held up by a belt. Such belts are known for instance from GB 2277865 and GB 2277866. These belts are held around a waist of a user by attachment means comprising a flexible strip of hook elements engaging with the belt material. Thus, a releasable hook and loop fastening arrangement is provided. The belt may be reused and does not have to be exchanged with every change of absorbent product.

Double sided hook patches are known as such, e.g. from FR 2830726, US 2010/0319167, and JP 2006325939. FR 2830726 discloses the use of a hook patch having a different number of hooks on each of its two different sides to achieve different attachment properties. The use of hook patches is disclosed in connection with various garments, including belts. US 2010/0319167 discloses a hook and loop fastening system comprising a double sided hook patch, the hook patch having different attachment properties on its two sides thanks to differently large areas of hooks on the two sides of the hook patch. The purpose of the system is to permit the hook patch to be removed prior to washing a relevant textile. JP 2006325939 discloses a double sided hook patch to be used in connection with diaper covers, clothes, and linen. The purpose of the double sided hook patch again, is to permit removal of the hook patch prior to washing a relevant textile.

Today, in connection with some absorbent products, a disposable belt including a length of belt material and a hook material patch is reused consecutively with a number of absorbent products until the disposable belt has become worn out, at which point the disposable belt is disposed of and a new disposable belt is used.

SUMMARY

It has been realized by the inventor that the length of belt material of a disposable belt for use with absorbent products often becomes worn out before the hook material patch of the disposable belt becomes worn out. Accordingly, it is desired to provide an economical, environmentally friendly disposable belt for use with absorbent products.

According to an aspect, a disposable belt for use with an absorbent product includes a length of belt material and a hook material patch connected to a first surface portion of the length of belt material. The length of belt material has a first major surface including the first surface portion and an opposite second major surface, and includes a loop surface structure. The hook material patch is flat and has a first side facing away from the first surface portion, and a second side abutting against the first surface portion of the length of belt material. The first side is provided with a first hook surface structure. The second side of the hook material patch is provided with a second hook surface structure, and the second hook surface structure engages with the loop surface structure of the length of belt material.

Since the hook material patch is attached to the length of belt material with the second hook surface structure, the hook material patch may be removed from the length of belt material when the latter has become worn out and may be attached to a new length of belt material to form a new disposable belt for use with an absorbent product. A natural resources-saving way of using disposable belts for use with absorbent products is thus achieved.

Herein, the terms—hook material, and hook surface structure—are to be interpreted to encompass the hook part of a hook and loop fastening system, e.g. known as a VELCRO® system. As such the "hooks" may have many different shapes which are adapted to engage with a loop part of the hook and loop fastening system. Purely as an example, J-shape, mushroom shape, and palm tree shape may be mentioned. Herein, the term—loop surface structure—is to be understood to encompass a surface structure to which a hook material of a hook and loop fastening system is attachable. Accordingly, a loop surface structure may include fibers or threads extending from a surface and back into the surface to define genuine loops, as well as a surface structure including fibers or threads extending out from a surface and having loose ends, which fibers or threads entangle with each other.

The disposable belt may be substantially flat and may be flexible such that it may be slung around the waist region of a user. The term—disposable belt—is to be interpreted to mean that such a belt is only usable for its intended purpose for a limited period of time, during which period it will become worn out. Such a limited period may be e.g. less than a week of use. In contrast, an ordinary belt, such as a belt used with garments e.g. pants, may be used over a much longer period of time before it becomes worn out, often over many years.

The disposable belt is a unit separate from the absorbent product with which it is to be used. As such, the disposable belt may be attached around a waist region of a user independently of a related absorbent product. Thus, the disposable belt may be used with a number of absorbent products, one after the other. An absorbent product to be used in conjunction with the disposable belt may be attachable to the disposable belt. The absorbent product may be attached to the disposable belt using hook material patches attached to the absorbent. product.

According to a further aspect a belt system for use with absorbent products comprises a disposable belt according to aspects and embodiments described herein and a second length of belt material, the second length of belt material having a loop surface structure.

Accordingly, the length of belt material of the disposable belt forms a first length of belt material of the belt system. Since the hook material patch is attached to the first length of belt material with the second hook surface structure, the hook material patch may be removed from the first length of belt material when the first length of belt material has become worn out and may be attached to a the second length of belt material to form a new disposable belt for use with an absorbent product. A natural resources-saving belt system for use with absorbent products is thus achieved.

Further features and advantages will become apparent when studying the appended claims and the following detailed description. Those skilled in the art will realize that different features may be combined to create embodiments other than those described in the following, without departing from the scope of the present invention, as defined by the appended claims.

BRIEF DESCRIPTION OF THE DRAWINGS

Various aspects, including particular features and advantages, will be readily understood from the following detailed description and the accompanying drawings, in which.

DETAILED DESCRIPTION

Embodiments of the present invention will now be described more fully with reference to the accompanying drawings, in which example embodiments are shown. However, this invention should not be construed as limited to the embodiments set forth herein. Disclosed features of example embodiments may be combined as readily understood by one of ordinary skill in the art to which this invention belongs. Like numbers refer to like elements throughout. Well-known functions or constructions will not necessarily be described in detail for brevity and/or clarity.

Figure 1:
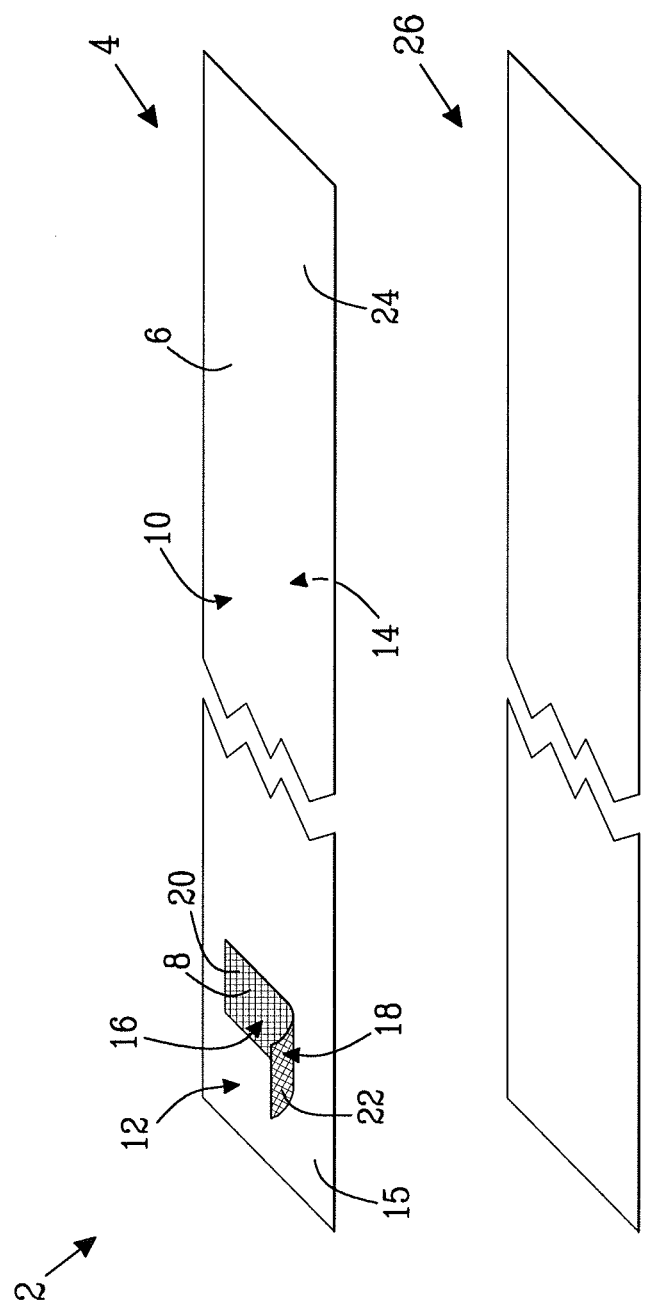
FIG. 1 illustrates a belt system for use with absorbent products and a disposable belt for use with an absorbent product.

FIG. 1 illustrates a belt system 2 for use with absorbent products and a disposable belt 4 for use with an absorbent product. The belt 4 may be slung around a waist of a user. To the belt 4 an absorbent product may be attached, e.g. by means of hook material patches provided on the absorbent product. The absorbent product may for example be designed as disclosed in the above mentioned GB 2277866.

The disposable belt 4 includes a length of belt material 6 and a hook material patch 8. For illustration purposes, the hook material patch 8 is illustrated only partially attached to the length of belt material 6. The length of belt material 6 has a first major surface 10 including a first surface portion 12 and a second major surface 14 opposite to the first major surface 10. The first surface portion 12 is arranged at a first end portion 15 of the length of belt material 6. The hook material patch 8 is connected to the first surface portion 12. The length of belt material 6 includes a loop surface structure. The length of belt material may include a nonwoven material. The hook material patch 8 is flat and has a first side 16 facing away from the first surface portion 12. The hook material patch 8 has a second side 18 abutting against the first surface portion 12. The first side 16 of the hook material patch 8 is provided with a first hook surface structure 20. The second side 18 of the hook material patch 8 is provided with a second hook surface structure 22.

The second hook surface structure 22 engages with the loop surface structure of the length of belt material 6. The disposable belt 4 is closed around the waist of a user by the first hook surface structure 20 engaging with the loop surface structure of the length of belt material 6 on the second major surface 14 at a second end portion 24 of the disposable belt. Accordingly, the first and second major surfaces 10, 14 of the length of belt material 6 each are provided with the loop surface structure.

According to embodiments, the length of belt material may include a material having a basis weight within the range of 60-160 gram/m$^2$. More particularly, the length of belt material may include a material having a basis weight of approximately 80 gram/m$^2$.

The length of belt material 6 suitably has a length to reach around a waist of an intended user. The width of the length of belt material 6 may be within the interval of 50-250 mm, or within the interval of 70-200 mm, or within the interval of 90-150 mm.

According to embodiments, the first hook surface structure 20 of the hook material patch 8 may be different from the second hook surface structure 22 of the hook material patch 8. Thus, the hook surface structures 20, 22 of the two sides 16, 18 may have different properties. For instance, the second hook surface structure 22 engaging with first surface portion 12 in the illustrated open position of the belt 4 may have stronger engaging properties than the first hook surface structure 20. In this manner, it may be ensured that the hook material patch 57 remains attached to the first surface portion 12 also after the disposable belt 4 has been closed and opened one or more times. Also, if the first and second major surfaces 10, 14 of a length of belt material 6 have different loop surface structures, different hook surface structures may adapt the hook material patch 8 to be securely attached to both of the different loop surface structures.

The first and second hook surface structures 20, 22 of the hook material patch 8 may be of the type provided in the VELCRO® HTH847 hook material. The hook density in the first hook surface structure 20 may be different from the hook density in the second hook surface structure 22.

The belt system 2 includes the disposable belt 4 including the length of belt material 6, which forms a first length of belt material 6 of the belt system 2. The belt system 2 further includes a second length of belt material 26. The second length of belt material 26 may be identical, or substantially identical, to the first length of belt material 6. In particular, the second length of belt material 26 includes a loop surface structure. In the belt system 2, the hook material patch 8 may be attached to the first length of belt material 6 already before the belt 4 is slung around the waist of a user.

The disposable belt 4 and the second length of belt material 26 of the belt system 2 may be provided from a dedicated dispenser for dispensing belts and lengths of belt material. Alternatively, the disposable belt 4 and the second length of belt material 26 of the belt system 2 may be provided in a package together with relevant absorbent products, or they may be provided in a dedicated separate package.

Figure 2:
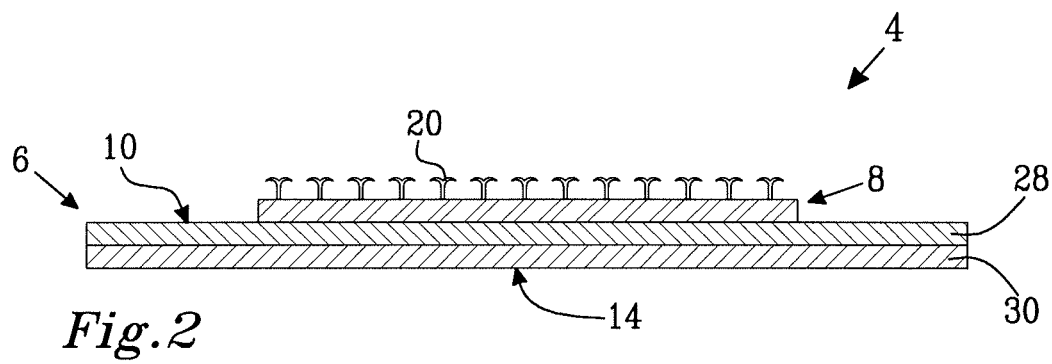
FIG. 2 illustrates schematically an end view of a disposable belt.

FIG. 2 illustrates schematically an end view of a disposable belt 4. The disposable belt 4 includes a length of belt material 6 having first and second major surfaces 10, 14, and a hook material patch 8. Again, first and second sides of the hook material patch 8 are provided with a first hook surface structure 20 and a second hook surface structure (not visible), respectively. The length of belt material 6 includes at least two layers having different properties. In the illustrated embodiments, a first layer 28 includes one kind of nonwoven material and a second layer 30 includes a different kind of nonwoven material. For example, the first layer 28 of the length of belt material 6 may include a carded nonwoven material and the first major surface 10. The second layer 30 of the length of belt material 8 may include a spunbond nonwoven material and the second major surface 14.

According to embodiments, the first hook surface 20 may have a hook density of 250-300 hooks/cm$^2$, and the second hook surface structure may have a hook density of 125-175 hooks/cm$^2$. The hooks as such may be shaped as discussed below in connection with FIGS. 3a and 3b. The second hook surface structure engages with the first layer 28 which includes the carded nonwoven material. As the disposable belt 4 is fastened around a waist of a user, the first hook surface structure 20 engages with the second layer 30 which includes the spunbond nonwoven material. With the hook density of 125-175 hooks/cm$^2$ of the second hook surface structure engaging with the carded nonwoven material and the hook density of 250-300 hooks/cm$^2$ of the first hook surface structure 20 engaging with the spunbond nonwoven material, a peel strength difference of more than 1 Newton between the engagement of the hook material patch 8 with the first layer 28 and the second layer 30 may be achieved for a hook material patch 8 having a size of approximately 13×35 mm. Accordingly, when the disposable belt 4 is opened to be removed from a waist of a user, the hook material patch 8 will remain attached to the first material layer 28 of the length of belt material 6. Put differently, an engagement between the second hook surface structure (22) and the first surface portion (12) has a first peel strength, and an engagement between the first hook surface structure (20) and the second major surface (14) has a second peel strength. The first peel strength exceeds the second peel strength by at least 1 Newton.

For a hook material patch 8 having a size of approximately 13×35 mm, the above-mentioned hook densities of the first and second hook surface structures also provide a shear strength of more than 25 Newton in the region of the hook material patch 8 when the belt is attached around the waist of a user. Thus, it may be ensured that the disposable belt 4, and a thereto attached absorbent product, remains attached to the user. Put differently, an engagement between the second hook surface structure (22) and the first surface portion (12), and an engagement between the first hook surface structure (20) and the second major surface (14) provides a shear strength of at least 25 Newton in a region of the hook material patch (8).

The length of belt material 6 may include the material Lamitex 80, provided by the company Fiberweb Tenotex.

Figure 3A:
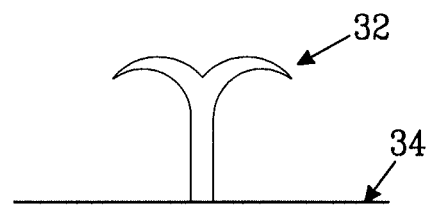
FIGS. 3a and 3b illustrate embodiments of hooks of hook surface structures of hook material patches.
Figure 3B:
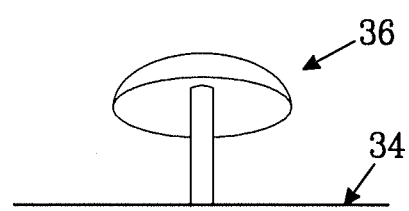

FIGS. 3a and 3b illustrate embodiments of hooks of hook surface structures of hook material patches according to embodiments. FIG. 3a illustrates a hook 32 having a back-to-back double J-shape structure, in which a stem of the double J-shape is bound to a surface 34 of the hook material patch and the curved parts of the double J-shape are arranged at a distance from the surface of the hook material patch. The back-to-back double J-shaped structure may sometimes be referred to as a palm tree structure. FIG. 3b illustrates a hook 36 having an umbrella shape. The umbrella shape may sometimes be referred to as a mushroom shape.

The height of the hooks 32, 36 may be approximately 0.35-0.40 mm.

Example embodiments described above may be combined as understood by a person skilled in the art. It is also understood by those skilled in the art that a spunbond nonwoven material may form the first layer 28 including the first major surface 10 and the first surface portion 12, and a carded nonwoven material may form the second layer 30 of a length of belt material 6 including at least two layers.

Although the invention has been described with reference to example embodiments, many different alterations, modifications and the like will become apparent for those skilled in the art. Therefore, it is to be understood that the foregoing is illustrative of various example embodiments and that the invention is defined only by the appended claims.

As used herein, the term "comprising" or "comprises" is open-ended, and includes one or more stated features, elements, steps, components or functions but does not preclude the presence or addition of one or more other features, elements, steps, components, functions or groups thereof.

The invention claimed is:

1. A disposable belt for use with an absorbent product, the disposable belt comprising:
a length of belt material having:
a first major surface and an opposite second major surface, each comprising a loop surface structure,
a first surface portion of the first major surface being arranged at a first end portion of the length of belt material, and
a second surface portion of the second major surface being arranged at a second end portion of the length of belt material; and
a hook material patch having:
a first side facing away from the first surface portion and having a first hook surface structure, and
a second side abutting against the first surface portion of the length of belt material and having a second hook surface structure, the second hook surface structure being adapted to engage with the loop surface structure of the first major surface at the first end portion,
wherein the disposable belt is adapted to be closed around a waist of a user by the first hook surface structure engaging with the loop surface structure of the second major surface at the second end portion of the disposable belt, and
wherein an engagement between the second hook surface structure and the first surface portion has a first peel strength, and an engagement between the first hook surface structure and the second major surface has a second peel strength, wherein the first peel strength exceeds the second peel strength.

2. The disposable belt according to claim 1, wherein the loop surface structure on each of the first major surface and the second major surface comprises the same material.

3. The disposable belt according to claim 1, wherein the length of belt material comprises a nonwoven material.

4. The disposable belt according to claim 1, wherein the length of belt material comprises a material having a basis weight within the range of 60-160 gram/m$^2$.

5. The disposable belt according to claim 1, wherein the length of belt material comprises a material having a basis weight of approximately 80 gram/m$^2$.

6. The disposable belt according to claim 1, wherein the length of belt material comprises at least two layers having different properties.

7. The disposable belt according to claim 6, wherein a first layer of the length of belt material comprises a carded nonwoven material and the first major surface, and wherein a second layer of the length of belt material comprises a spunbond nonwoven material and the second major surface.

8. The disposable belt according to claim 1, wherein the hook material patch comprises hooks having an umbrella shape, or a back-to-back double J-shape structure, in which a stem of the double J-shape is bound to a surface of the hook material patch and the curved parts of the double J-shape are arranged at a distance from the surface of the hook material patch.

9. The disposable belt according to claim 1, wherein the first hook surface has a hook density of 250-300 hooks/cm$^2$, and the second hook surface structure has a hook density of 125-175 hooks/cm$^2$.

10. A belt system for use with absorbent products, the system comprising a disposable belt according to claim 1 and a second length of belt material, the second length of belt material comprising a loop surface structure, the second length of belt material being adapted to form a disposable belt together with the hook material patch.

11. A disposable belt for use with an absorbent product, the disposable belt comprising:
   a length of belt material having:
      a first major surface and an opposite second major surface, each comprising a loop surface structure,
      a first surface portion of the first major surface being arranged at a first end portion of the length of belt material, and
      a second surface portion of the second major surface being arranged at a second end portion of the length of belt material; and
   a hook material patch having:
      a first side facing away from the first surface portion and having a first hook surface structure, and
      a second side abutting against the first surface portion of the length of belt material and having a second hook surface structure, the second hook surface structure being adapted to engage with the loop surface structure of the first major surface at the first end portion,
   wherein the disposable belt is adapted to be closed around a waist of a user by the first hook surface structure engaging with the loop surface structure of the second major surface at the second end portion of the disposable belt, and
   wherein the first hook surface structure of the hook material patch is different from the second hook surface structure of the hook material patch.

12. The disposable belt according to claim 11, wherein the first hook surface has a hook density of 250-300 hooks/cm$^2$, and the second hook surface structure has a hook density of 125-175 hooks/cm$^2$.

13. The disposable belt according to claim 11, wherein the loop surface structure on each of the first major surface and the second major surface comprises the same material.

14. The disposable belt according to claim 11, wherein the length of belt material comprises a nonwoven material.

15. The disposable belt according to claim 11, wherein the length of belt material comprises a material having a basis weight within the range of 60-160 gram/m$^2$.

16. The disposable belt according to claim 11, wherein the length of belt material comprises a material having a basis weight of approximately 80 gram/m$^2$.

17. The disposable belt according to claim 11, wherein the length of belt material comprises at least two layers having different properties.

18. The disposable belt according to claim 17, wherein a first layer of the length of belt material comprises a carded nonwoven material and the first major surface, and wherein a second layer of the length of belt material comprises a spunbond nonwoven material and the second major surface.

19. The disposable belt according to claim 11, wherein the hook material patch comprises hooks having an umbrella shape, or a back-to-back double J-shape structure, in which a stem of the double J-shape is bound to a surface of the hook material patch and the curved parts of the double J-shape are arranged at a distance from the surface of the hook material patch.

20. A belt system for use with absorbent products, the system comprising a disposable belt according to claim 11 and a second length of belt material, the second length of belt material comprising a loop surface structure, the second length of belt material being adapted to form a disposable belt together with the hook material patch.

* * * * *